United States Patent [19]

Moran et al.

[11] Patent Number: 4,947,351

[45] Date of Patent: Aug. 7, 1990

[54] ULTRASONIC SCAN SYSTEM FOR NONDESTRUCTIVE INSPECTION

[75] Inventors: Thomas J. Moran, Huber Heights; Charles F. Buynak, Kettering; Richard W. Martin, Springboro, all of Ohio

[73] Assignee: The United States of America as represented by the Secretary of the Air Force, Washington, D.C.

[21] Appl. No.: 191,303

[22] Filed: May 6, 1988

[51] Int. Cl.⁵ .................... G06F 15/20; G01N 9/24
[52] U.S. Cl. ................................. 364/507; 364/550; 364/508; 73/602; 73/606; 73/607
[58] Field of Search .............. 364/507, 413.25, 508, 364/550, 551.01; 73/626, 628, 598, 600, 602, 606, 607; 128/660; 382/8; 367/88

[56] References Cited

U.S. PATENT DOCUMENTS

| | | | |
|---|---|---|---|
| 3,868,847 | 3/1975 | Gunkel | 73/67.8 |
| 3,940,952 | 3/1976 | Mitchell | 73/67.8 |
| 3,955,405 | 5/1976 | Couture | 73/67.7 |
| 3,972,228 | 8/1976 | Mansson | 73/67.7 |
| 3,977,236 | 8/1976 | Raatz, Jr. et al. | 73/67.8 |
| 3,999,422 | 12/1976 | Lehmann et al. | 73/67.8 |
| 4,033,176 | 7/1977 | Eberle et al. | 73/67.9 |
| 4,033,177 | 7/1977 | Case | 73/67.9 |
| 4,068,524 | 1/1978 | Lewis et al. | 73/598 |
| 4,074,564 | 2/1978 | Anderson | 364/413.19 |
| 4,089,225 | 5/1978 | Kraska et al. | 73/614 |
| 4,089,226 | 5/1978 | Kraska et al. | 73/614 |
| 4,092,867 | 6/1978 | Matzuk | 73/609 |
| 4,100,808 | 7/1978 | Evans et al. | 73/588 |
| 4,102,205 | 7/1978 | Pies et al. | 73/626 |
| 4,106,346 | 8/1978 | Matzuk | 73/67.8 |
| 4,137,776 | 2/1979 | Rudis et al. | 73/611 |
| 4,271,707 | 6/1981 | Lakin | 73/614 |
| 4,333,345 | 6/1982 | Renzel et al. | 73/606 |
| 4,364,274 | 12/1982 | Sharpe | 73/615 |
| 4,375,671 | 3/1983 | Engle | 364/413.25 |
| 4,403,509 | 9/1983 | Kretz | 73/626 |
| 4,432,235 | 2/1984 | Renzel et al. | 73/611 |
| 4,472,973 | 9/1984 | Sugai et al. | 73/626 |
| 4,543,827 | 10/1985 | Tominaga et al. | 364/508 |
| 4,593,314 | 6/1986 | Siler | 364/413.25 |
| 4,768,155 | 8/1988 | Takishita et al. | 364/507 |
| 4,794,545 | 12/1988 | Salvado | 364/497 |
| 4,803,638 | 2/1989 | Nottingham et al. | 364/507 |
| 4,817,015 | 3/1989 | Insana et al. | 364/413.25 |
| 4,817,016 | 3/1989 | Thompson et al. | 73/598 |

OTHER PUBLICATIONS

IBM Technical Disclosure Bulletin; "Method of Increasing the Resolution of Medical Ultrasound B-mode Images" 30/6, 11/87.

"Characteristics of Impact Damage in Composites" by C. F. Buynak and T. J. Moran, SAMPE Journal, Mar.-/Apr. 1988, vol. 24, No. 2

*Primary Examiner*—Parshotam S. Lall
*Assistant Examiner*—Ellis B. Ramirez
*Attorney, Agent, or Firm*—Gerald B. Hollins; Donald J. Singer

[57] ABSTRACT

An ultrasonic echo scanning apparatus having operator determined software controlled gated sampling of individual radio frequency excursions in the reflected ultrasonic energy waveform. Use of the system to obtain heretofore images of damage layers, resident in close physical proximity to large echo regions of a workpiece and images of good correlation with physical inspection of a disintegrated workpiece is also disclosed.

22 Claims, 6 Drawing Sheets

ULTRASONIC SCAN SYSTEM FOR NONDESTRUCTIVE INSPECTION

RIGHTS OF THE GOVERNMENT

The invention described herein may be manufactured and used by or for the Government of the U.S. for all governmental purposes without the payment of any royalty.

MICROFICHE APPENDIX

The present document includes a microfiche appendix in which 162 pages of computer program listing and information relating thereto are reproduced. The appendix is contained on two fiche of format Al microfiche of the 98 frame, 14 column, by 7 row, variety and includes the 162 pages of text along with three pages of formal information.

BACKGROUND OF THE INVENTION

This invention relates to the field of nondestructive testing in which a test specimen or workpiece is illuminated with acoustic wave energy and the ultrasonic frequency energy echo returns therefrom are processed for the purpose of feature mapping, locating, and identification.

The use of ultrasonic energy reflections to "view" the internal features of an integral workpiece has been known in the art for a number of years. As heretofore practiced, however, this use of ultrasonic energy viewing has been limited in resolution capability, especially with respect to workpiece features which are located physically adjacent a prominent feature of the workpiece-features such as its frontal or rearward surfaces. Although a portion of this limitation may be attributable to the somewhat elementary capability of available waveform processing apparatus in the electronic arts, a major portion of this limitation is believed related to processing of the available ultrasonic echo information according to a less than optimum information processing arrangement—an arrangement tending to overlook or obscure some available information.

SUMMARY OF THE INVENTION

In the present invention, the waveform of ultrasonic energy echo reflections is processed in accordance with a digital high resolution but memory conserving arrangement which enables location, viewing, identification, size appraisal, and other activities relating to workpiece physical features. These activities may be generically referred to as workpiece mapping.

The images obtained with the processing of the invention enable high resolution mapping of such physical phenomenon as impact damage and layer separations in a laminate workpiece, for example, an aircraft exterior surface sample—notwithstanding the proximity of the mapped region to workpiece regions of large ultrasonic signal generation character. The invention also includes provisions for accommodating such real world workpiece characteristics as surface roughness and surface inclinations to a plane of scanning and variations in workpiece composition. The invention further includes a space conserving data storage arrangement and the signal processing flexibility to optimize an achieved mapping of physical features.

It is an object of the present invention therefore to provide an acoustic waVe inspection arrangement wherein the mapping of workpiece features located in close physical proximity with other unwanted and cluttering workpiece features may be accomplished.

It is another object of the invention to provide an acoustic wave energy inspection apparatus wherein the information received in reflected acoustic wave signals is more fully utilized.

It is another object of the invention to provide an acoustic wave energy inspection apparatus wherein more optimum samples of the acoustic wave signal are generated and retained in information storage.

It is another object of the invention to provide an acoustic wave energy inspection arrangement wherein common physical characteristics of an inspected workpiece are readily accommodated.

It is another object of the invention to provide an acoustic wave energy inspection arrangement which is well suited for inspecting laminate structures.

It is another object of the invention to provide an acoustic wave energy inspection arrangement which is capable of detecting lamina separations and other indicia of destructive testing.

It is another object of the invention to provide an acoustic wave energy testing waveform processing arrangement that is useful with the graphite-epoxy and other composite materials for future generation military aircraft.

It is another object of the invention to provide an improved acoustic wave energy inspection arrangement in which a major portion of the signal processing operations can be embodied as electronic circuitry hardware or as software usable with a general purpose digital computer.

It is another object of the invention to provide an acoustic wave energy inspection arrangement in which improved physical property mapping is achieved notwithstanding the frequency response and other limiting factors imposed by an acoustic energy to electrical energy transducer.

It is another object of the invention to provide an acoustic wave mapping arrangement which affords a desirable degree of accommodation for a variety of workpiece dimensions, composition and physical configurations and location.

It is another object of the invention to provide an acoustic wave ultrasonic energy mapping arrangement which provides a high degree of results correlation with the physical parameters of a workpiece.

Additional objects and features of the invention will be understood from the following description and the accompanying drawings.

These and other objects of the invention are achieved by an ultrasonic mapping apparatus which includes a transducer for illuminating a selected portion of a workpiece with a scanning raster having pulses of acoustic energy of first time interval separation between the points comprising each raster line and for sensing the ultrasonic frequency ringing waveform energy return echoes from the pulses of acoustic energy during an echo time interval following each illuminating pulse; apparatus for sampling the individual excursions of the ringing waveforms during a plurality of number identifiable data acceptance window gates of second time interval width and third time interval successive separations during each echo time interval following the illuminating pulses, the sampling including digitizing a predetermined number of segregated waveform values within each said window gate; apparatus for generating from the plurality of waveform values in each window gate, and in accordance with a predetermined value consolidation algorithm, a pixel value representative of the plurality of waveform values in the window gate; apparatus for altering the parameters of the process, including the workpiece portion selected for illumination, the time duration of the illuminating pulses, the number of digitized waveform values in each window gate, the duration of the first second and third time intervals and the nature of the value consolidation algorithm, in iterative sequence until an optimum view of selected workpiece details including sub-surface defects obtains; the apparatus for altering including apparatus for viewing assembled, same gate identifying number, images of said pixels; and apparatus for recording and identifying optimized pixel images.

DETAILED DESCRIPTION

Figure 1:
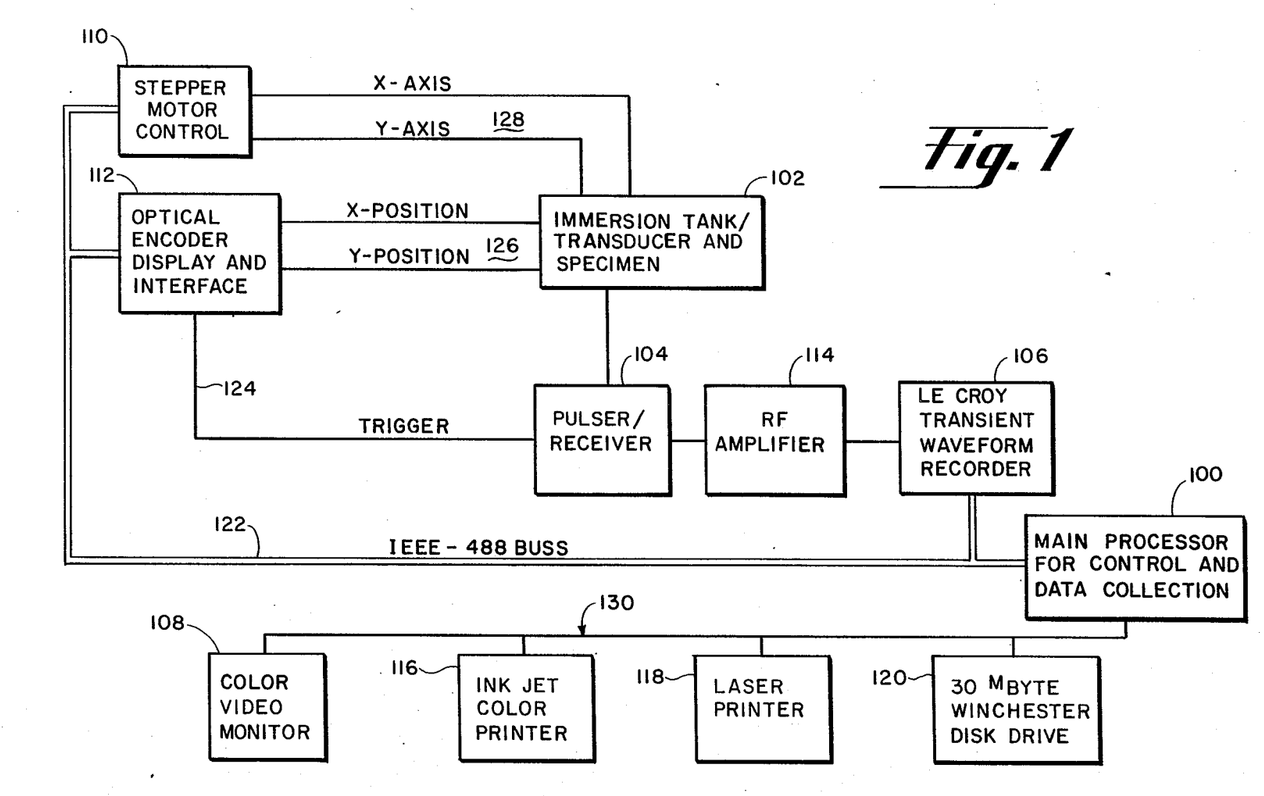
FIG. 1 shows an overall block diagram of an acoustic wave resting system made in accordance with the invention.

FIG. 1 in the drawings shows a block diagram of an acoustic wave echo ultrasonic inspection system is made in accordance with the present invention. The FIG. 1 apparatus is capable of generating multi-layer ultrasonic "sonograms" which indicate in detail the nature of internal features of a workpiece. The FIG. 1 system is particularly capable of representing details which were heretofore obscured in prior art sonograms and accomplishes this task by way of utilizing information which was lost in prior signal processing arrangements.

Figure 2:
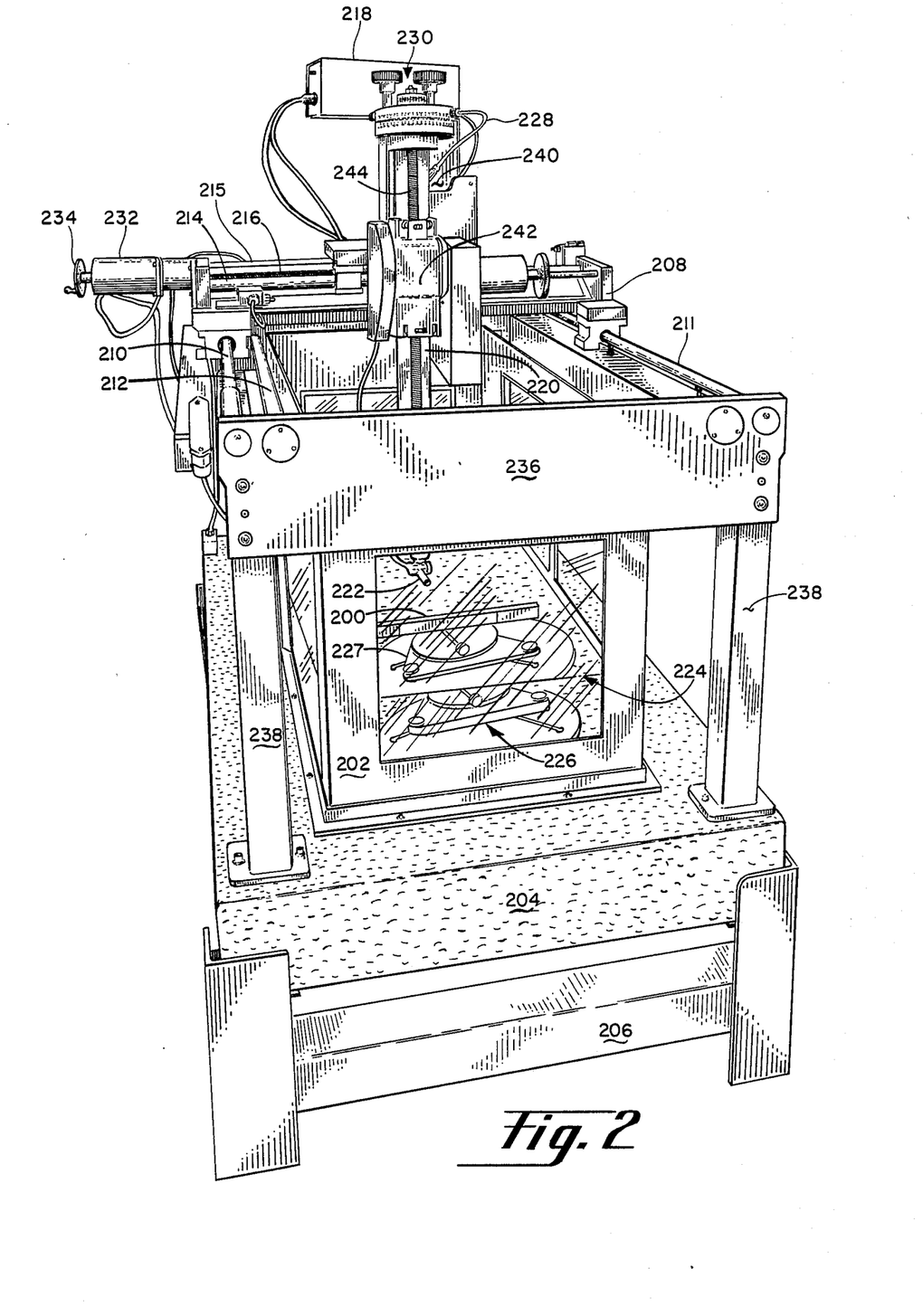
FIG. 2 shows details of a workpiece mounting and scanning apparatus which may be used with the FIG. 1 system.

In the FIG. 1 system, a specimen to be examined, a segment of a multi-layered graphite epoxy aircraft fabrication sheet damaged by a controlled energy impact, for example, is received in a sample holding immersion tank 102. In addition to the specimen or workpiece, the tank 102 also contains an electrical energy to acoustic energy transducer device which is preferably of the bilateral or both electrical to acoustic and acoustic to electrical energy conversion capability. The specimen or workpiece to be examined is disposed within the acoustic field of the transducer in the tank 102 and acoustic coupling between transducer and specimen is enhanced through the use of a liquid ultrasonic energy transmitting medium such as water, preferably distilled water. Additional details of the lank 102 and the transducer and specimen received therein are shown in FIG. 2 of the drawings.

Also shown in the FIG. 1 diagram is a two-axis positioning and scanning apparatus by which the transducer in the tank 102 is located in a suitable position and moved in predetermined scanning motion with respect to the workpiece specimen. Mechanical information from the positioning and scanning apparatus is related to the transducer in the tank 102 by way of mechanical linkage which is indicated at 128 in FIG. 1. The achieved two-axis position of the transducer is represented as electrical signals by way of an optical encoder which may also have display and interface capabilities and is indicated at 112 in FIG. 1. Signals for controlling the stepping motors of the two-axis positioning and scanning system 110 and signals generated by the optical encoder 112 originate in and terminate in respectively a central computer which is indicated at 100 in FIG. 1

The computer 100 may, for example, be of the PDP 11/23 type and be equipped with a 30 megabyte Winchester hard disk as is shown at 120 in FIG. 1. The PDP 11/23 is a general purpose digital computer which is manufactured by Digital Equipment Corporation of Maynard, Mass., and herein is provided with an operating system capable of receiving program commands in the version of the Fortran programming language version number 4.2.

Communication between the computer 100 and the positioning related apparatus of blocks 110 and 112 and also between the computer 100 and the specimen data generated by a transient waveform recorder 106 occurs by way of a communication bus which may be of the Institute of Electrical and Electronic Engineers (IEEE) type 488 or an equivalent bus arrangement.

Pulses of ultrasonic energy capable of "illuminating" the sample received in the tank 102 originate in a pulser/receiver circuit 104 in FIG. 1 with pulse initiation occurring in response to the specimen coming to transient rest in a pr ®determined position—as is indicated by a trigger pulse flowing along the path 124 in FIG. 1. Electrical signals generated by the acoustic energy reflected from the specimen in the tank 102 are coupled to the RF amplifier 114 by the pulser/receiver 104 for amplification. These ultrasonic echo originating signals tend to have a damped ringing waveform. This waveform is in response to an impulse or brief duration large amplitude acoustic energy illuminating pulse generated by the transducer in response to a similar electrical pulse generated by the pulser/receiver 104.

The pulser receiver circuit 104 accomplishes segregation of illuminating and echo pulse waveforms using signal limiting shunt diodes in a manner which is know in the electrical art. An apparatus suitable for use as the pulser/receiver circuit 104 is the Model 5052PR transducer which is manufactured by Panametrics Inc., located in Waltham, Mass. The radio frequency amplifier 114 may be of a type AWL-500M which is manufactured by Avantek Inc. of Santa Clara, Calif.

An important element of the FIG. 1 system is represented by the transient waveform recorder 106. The recorder 106 is generally in the nature of a combined high speed analog to digital converter and scratch pad or temporary memory storage apparatus. For use in the present invention, a transient waveform recorder of the type TR8828B with memory module model MM8103A and GP1b interface module model 8901A all of which may be mounted in enclosure model 8013A, which is manufactured by LeCroy Inc, of Spring Valley, N.Y., and which generally provides a 222 megahertz data sampling rate with an 8 bit or 256 discrete level resolution capability, is preferred.

The LeCroy or an equivalent transient waveform recorder receives ringing radio frequency signals having a fundamental frequency that is in the range of five to ten megahertz from the transducer in the tank 102 and the pulser/receiver 104. This transducer frequency band is typical, frequency bands within the range of 100 K kilohertz to 25 megahertz are feasible, however. Such frequencies are in the high radio frequency portion of the electromagnetic spectrum. The transient waveform recorder provides an IEEE-488 bus compatible digital output signal for transmission to the computer 100.

Information processed by the computer 100 is communicated along a second bus 130 to a selected one or more of the indicated display output devices, a video color monitor 108 an ink jet color printer 116 or a laser printer 118. The bus 130 also serves as a communication link between the computer and the data storage of the disk 120.

Figure 4:
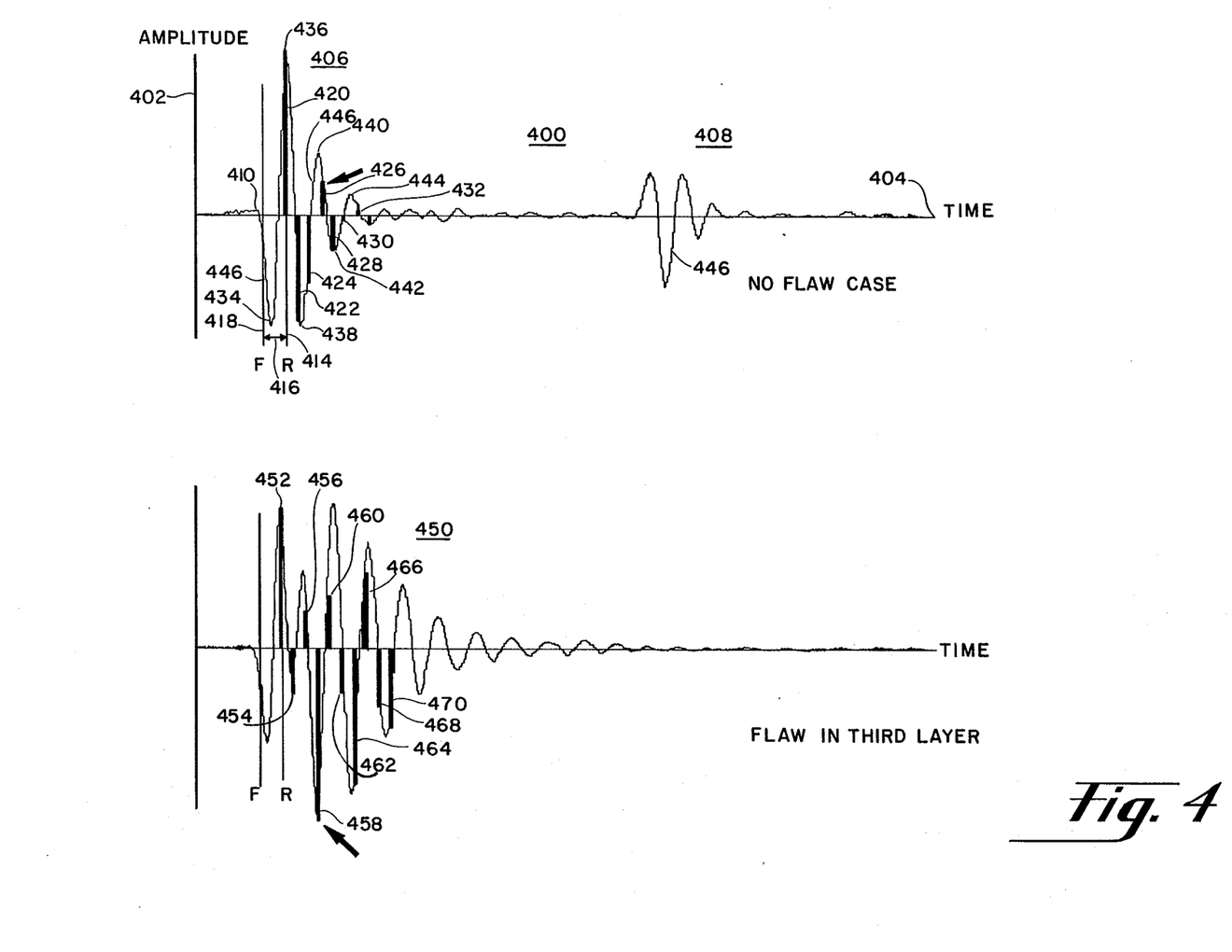
FIG. 4 shows two sonic wave signals processed in accordance with one aspect of the invention.

The signal processing accomplished in the computer 100 is also an important aspect of the present invention and is described in some detail in connection with the waveforms of FIG. 4 and is additionally described in programming language form in the software listed in the microfiche appendix hereto. Other references to the microfiche appendix and discussion of its contents appear in later sections of this description One physical arrangement for several of the major elements appearing in the FIG. 1 acoustic wave ultrasonic inspection system is shown in FIG. 2 of the drawings. In FIG. 2, the immersion tank, which was represented at 102 in FIG. 1, is shown at 202 and the specimen being inspected or mapped is shown at 200 along with the bilateral transducer performing the inspection or mapping is indicated at 222 in FIG. 2. Additional elements shown in FIG. 2 include a suspended mass 204 and mounting frame therefor 206, which serve to isolate the test specimen and transducer from vibrations or other disturbing noise. The mounted mass 204 may consist of a block of granite, concrete, steel or other massive material; this block is suspended on compressed air cushions or other vibration isolation elements which are not shown in FIG. 2 but are disposed between the frame 206 and the mass 204. Above the mass 204 and surrounding the tank 202 in the FIG. 2 apparatus, is a frame member 236 which includes a pair of horizontal way members 210 and 211 and a set of legs 238 which are mounted on the mass 204.

A horizontal carriage member 208 is suspended on the way members 210 and 211 and is positioned therealong by a rotationally drivable lead screw member 212. The lead screw member 212 is rotated by a driving arrangement such as a stepping motor in order to position the carriage member 208 in a desired position with respect to the tank 202 and also in order to move the transducer 222 in a scanning motion when desired. The lead screw driving mechanism is not shown in FIG. 2 but may be of a similar arrangement to the stepping motor apparatus 232 which drives the lead screw 216 in order to position a head member 242 along the carriage member 208 and perform scanning in the workpiece orthogonal direction as needed. The stepping motor 232 and lead screw 216 may also provide scanning movement of the head 242 along a pair of orthogonal way members 214 and 215. Manual positioning of the lead screw 216 is provided by way of a hand crank 234. A mounting arm 220 and third lead screw member 244 are suspended from the head member 242 for the purpose of carrying the transducer element 222. The third lead screw member 244 is driven from a knob and vernier scale apparatus 230 in order to accurately position the transducer member 222 in the vertical direction.

Also shown in FIG. 2 are the liquid level line 224 within the tank 202, the specimen mounting and positioning apparatus 226 which is immersed in the tank liquid along with the specimen 200. A second fainter image of the mounting and positioning apparatus 226 appears at 227 in FIG. 2 and results from the optical diffraction effects of the water and glass of the tank 202. Additionally shown in FIG. 2 are the enclosures 218 and 240 for the pulser receiver 140 and radio frequency amplifier 114 that were described in FIG. 1. A multiple axis movement apparatus of the FIG. 2 type which includes elements such as the mounting frame 206, the horizontal carriage member 208, the head member 242 and the mounting arm 220, is manufactured by Ketco, Inc. which is located in Beavercreek, Ohio, and was custom manufactured. This custom fabricated apparatus or alternately commercially available equivalents thereof or other arrangements may be used in other embodiments of the scanning apparatus.

Although the relationship between the transducer 222 and the specimen 200 is made to be flexible in the FIG. 2 apparatus, it is preferable in scanning a non-metallic laminate aircraft surface sample, for example, that the transducer element 222 be located about 50 to 75 millimeters or two to three inches from the specimen 200 and disposed at an angle of 90° with respect to the specimen surface. Other spacings and angles are possible depending upon the transducer and materials involved. Scanning motion preferably involves an overall scan length of equal to the extent of the damage zone to be inspected and a movement velocity of approximately one inch per second or 25 millimeters per second with transient stops of fractions of a second for acoustic pulse transmission and reception.

The transducer element 222 is preferably of the focused acoustic energy type having a focal length of 50–150 millimeters or two to six inches and a characteristic frequency in the five to 10 megahertz range. A type 146–280, 10 megahertz, 150 millimeters or three inch focus transducer manufactured by KB-Aerotech Inc. located in Lewiston, Pa., is suitable.

The FIG. 2 apparatus provides a convenient and adjustable laboratory arrangement for accomplishing scanned ultrasonic illumination and echo collection from a test specimen which is immersed in an acoustic energy coupling fluid. In the FIG. 2 arrangement, the dimensions and angles and other parameters associated with the transducer to specimen interface are both adjustable and reasonably stable in an elected condition. Other scanning arrangements may, of course, be desirable especially to enable use of the invention apparatus in a working environment such as, for example, might be desirable in an aircraft maintenance facility where damaged aircraft skin structure is to be evaluated.

Signal Processing

Figure 3:
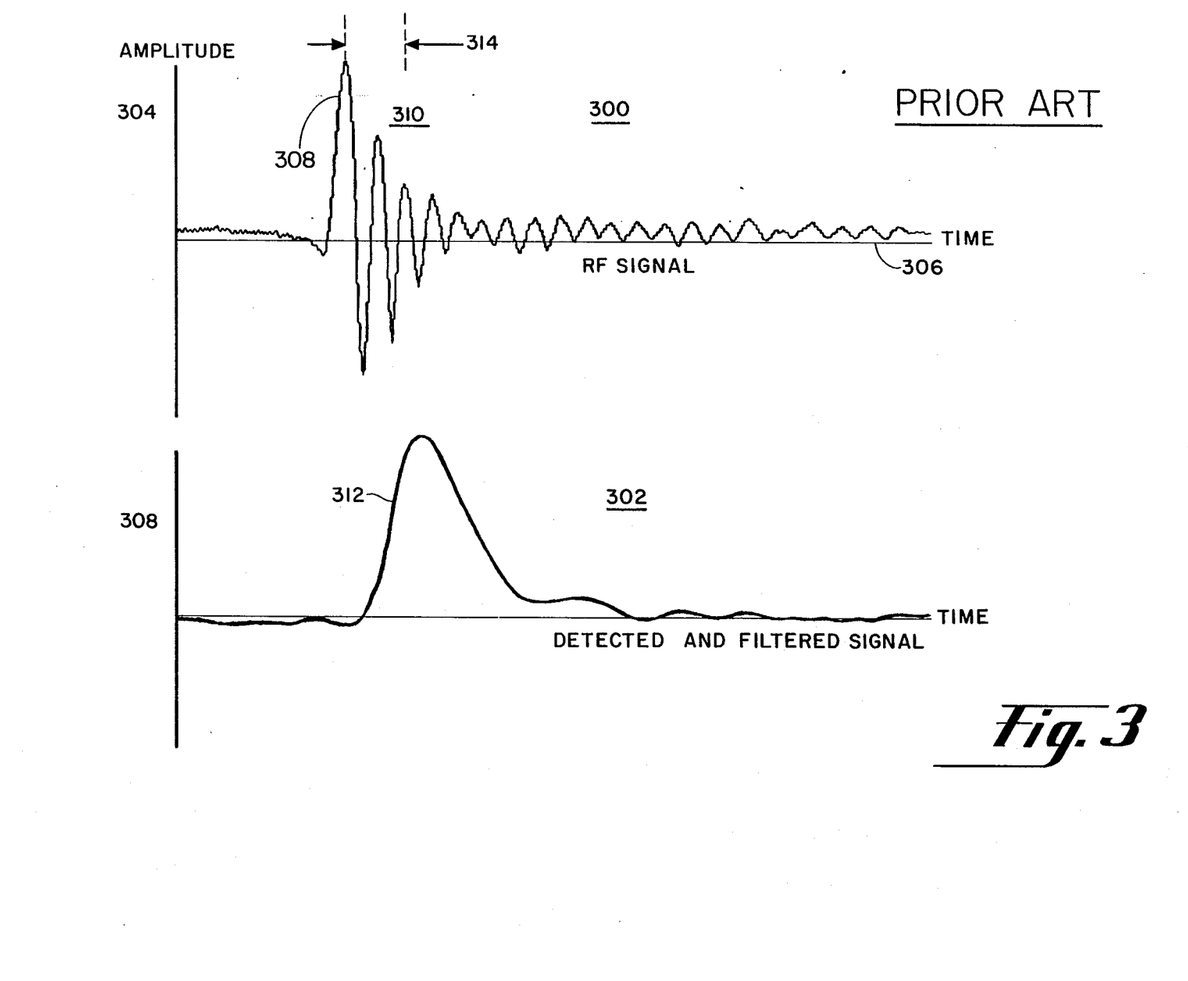
FIG. 3 shows a sonic wave echo waveform before and after being processed in accordance with prior art signal processing.

FIG. 3 in the drawings illustrates a prior art signal processing arrangement which has been used with apparatus of the FIG. 1 and FIG. 2 type. At 300 in FIG. 3 is shown an unprocessed amplitude vs. time display of a radio frequency signal waveform 308 which may originate in the ultrasonic frequency acoustic reflections from a workpiece. The FIG. 3 signal 300 is shown displayed along a pair of coordinate axes 304 and 306. In FIG. 3, the portion 310 of the radio frequency signal waveform 308 represents an ultrasonic energy reflection from a physical feature of the workpiece being examined—a reflection such as might occur from the frontal or scanned surface of the workpiece. The subsequent portions of the waveform 308 in FIG. 3 indicate the presence of nearly homogeneous material having minimal signal reflection physical features.

In prior art processing of the waveform 308, it has been common practice to detect and filter the waveform carrier and utilize the information contained in the waveform envelope for image presentations—such in the manner of the detector and filter network used in an amplitude modulated (AM) radio receiver. The information resulting from this envelope detection and filtering of the waveform 308 is represented at 312 in the view 302 of FIG. 3. According to this prior art signal processing rationale, it is desirable to rectify the pulses of the waveform 300 and to employ the rectified or detected pulses as the input signal to an electrical filter network. The detected and filtered envelope of the waveform 308 is then used as the information source for a display or signal analysis apparatus. This type of signal processing is used in order that noise transient and individual waveform perturbations which are difficult to interpret be removed in favor of obtaining a smooth and more easily comprehended waveform of the type shown at 312 in FIG. 3. As indicated at 314 in FIG. 3, this prior art signal processing often involves a time delay as a result of the filtering applied.

Although the waveform as shown in 302 in FIG. 3 conveys an easily understood meaning with respect to, for example, the frontal or scanned surface of a workpiece. It has been found that processing of this type is not optimum and indeed tends to obscure a significant degree of useful information that resides in the radio frequency waveform 308. Particularly this processing obscures the fine detail or high frequency signal waveform components and is so slow in nature as to hide workpiece features located in close physical proximity with string signal sources in the workpiece. The time constant of the electrical reactance components used in the filter network is notably troublesome in this regard.

In lieu of the detection and slow filtering which provide the waveform 312 in FIG. 3, it has been found that processing which considers the rapid transient excursions of the radio frequency waveform 308 in FIG. 3, processing having a degree of sophistication adequate to extract information from the waveform 308 without also requiring the large amount of memory or storage capability necessary for a complete remembering or reconstruction of the waveform 308 is indeed a realizable possibility. The essence of one processing arrangement that is capable of accomplishing this improved information extraction in combination with moderate storage requirements is shown in FIG. 4 of the drawings.

Two radio frequency waveforms resulting from ultrasonic energy reflections from physical features of a workpiece are shown at 400 and 450 in the FIG. 4 drawing. The waveform 400 includes two major reflection areas 406 and 408 such as might result, for example, from the frontal surface and back surface of a workpiece. The waveform 400 is plotted along axes representing amplitude and time as is indicated at 402 and 404 in FIG. 4. The waveforms 400 and 405 are realized using a focused ultrasonic transducer having a relatively long focal length, in the range of 75 to 150 millimeters, in order that good lateral resolution may result. The fundamental frequency of the waveform 400 is in the five to ten megahertz frequency range.

The waveform 400 includes an initial departure from quiescence at 410, a first negative going peak at 434 and subsequent polarity alternating and amplitude varying peaks at 436, 438, 440, 442, 444, and so on. The initial practical measurable departure point 418 of a waveform relating to a frontal surface reflection is used as a point of time reference in the processing described below. Parenthetically, it may be noted that the phase (polarity) of the peaks in each reflection area of a waveform is also of information bearing significance in a signal processing system since the phase (polarity) of individual peaks is indicative of the signal velocity changes occurring at the interface of two different ultrasonic energy conducting mediums: that is, the phase (polarity) of the waveform swing is dependent on the relative magnitude of velocity indicating variables in a $(V_1-V_2)$ mathematical expression—as is known in the sonic wave testing art.

According to one aspect of the present invention, it is found that a significantly greater degree of information can be obtained from a waveform of the type 400 in FIG. 4 in comparison with the processing of FIG. 3 through the use of carefully placed sampling or gating windows along excursions of the waveform. In addition to the placement of these sampling windows, the window width or the time length of these windows and the number of samples of the waveform are also important in the extraction of information. The location and duration of these sampling or gating windows with respect to the FIG. 4 waveform 400 is indicated by the heavy, dark positive and negative lines in the FIG. 4 waveforms. In addition to the horizontal positioning of these sampling or gating intervals in the FIG. 4 waveforms, the length of the heavy, dark lines as is indicated at 420, 422, 424, 426, and 428 in FIG. 4 is representative of the waveform value obtained during the sample window—according to some predetermined waveform to sample relationship criteria as is described subsequently herein. In view of the significance of the location and timing of these samples, an arrangement allowing operator viewing of a representative waveform during placement of the sampling pulses is in accordance with the invention.

It is convenient to perform the FIG. 4 signal processing through the use of a programmed general purpose digital computer which receives digital signals representing the ultrasonic waveform to be processed from a transient waveform recorder as was described in connection with FIG. 1 above. In this waveform recorder and digital computer combination it is desirable to temporarily store in memory in the waveform recorder a large number of digital values representing the waveform 400 with a high degree of resolution and to communicate this high resolution data to the computer 100 where the window gate placement and value determinations for the samples indicated by the line lengths 420, 422, 424, 426 and 428 are accomplished. Storage of these samples on the disk 120 for permanent retention and for displaying of identified physical features using the monitor 108 the printer 116 or the printer 118 of FIG. 1 is also accomplished in the computer 100. By way of this two-step waveform recorder and computer arrangement, a desirable combination of the high speed unsophisticated capabilities available in transient waveform recorder instruments, such as above mentioned LeCroy apparatus is advantageously combined with the intelligent slower speed capabilities which can be incorporated into software programming of the computer 100.

As is indicated by the steps or irregularities 446 in the waveform 400 of FIG. 4, this waveform has, in fact, been transient recorded in a device such as the above described Lecroy instrument. In the LeCroy instrument, sampling rates in the range of 200 megahertz or five nanoseconds per sample are obtainable; with the data observed during this high speed sampling being temporarily storable in RAM memory of 64 kilobyte overall capability. Samples taken at this rate in the five to ten megahertz transducer ringing waveform of FIG. 4 result in the pulse irregularities shown at 446 in FIG. 4 for each of the ringing sinusoid components. Transfer of this temporarily stored information by way of the IEEE-488 bus 122 in FIG. 2 to the computer 100 may occur in the form of 512 words of eight bits each and require a total of some 2048 microseconds of transferring time. As is indicated by the waveforms at 400 and 450 in FIG. 4 this capturing and transferring capability provides a meaningful and relatively undistorted view of the ultrasonic energy reflection.

Once the high resolution digital data from the recorder 106 is available for computer analysis, the generation of window gate samples of selected location and width with respect to the waveform information can occur. It is found desirable in this process to provide a wide range of flexibility and to provide for human operator judgment input in selecting the sample locations and waveform to sample amplitude relationships for storing the ultrasonic energy waveforms. In the software used in the computer 100 for analyzing the waveforms 400 and 450 in FIG. 4, for example, this large degree of flexibility appears as the capability for an operator to select the number and the time duration of the gate window samples to be stored for a particular waveform. As is indicated in the subroutine MENUA and the subroutine SPECG of this software, provision is made for an operator to select the center position of one or a number of sampling gates and to select the width or time duration of one or a number of gates and to select the same or different spacings between sample gates.

In order for an operator to position the gates which obtain the data samples shown at 420-428 in FIG. 4, it is desirable to locate these samples with respect to a waveform feature that is identifiable and early located in each waveform to be processed. A convenient identification point for this purpose is the above discussed departure of the waveform from quiescent value in response to the initial reflection of sonic energy from the front surface of the workpiece—as is indicated at 410 in FIG. 4. The front surface identification line 418 in FIG. 4, which is also indicated by the letter F, designates the frontal surface echo point selected by the operator of the FIG. 4 waveforms to serve as the basic point of reference for sample window gate location. Following this basic reference point, it is desirable to wait a determined period of time, the delay interval indicated at 416 in FIG. 4 prior to locating the first sampling gate. The duration of the delay interval 416 is selected to permit the first sampling gate to be centered on the largest peak which in this case is the first positive polarity peak in the waveform 400. In the FIG. 4 representation, the periodic sampling gate program option is used with the first gate occurring at the end of the delay interval 416, at the time indicated by the line 414, the line R, and successive gates are disposed at periodic intervals thereafter. The letter R indicates the line 414 to be a reference point—the centerline of the first window gate in FIG. 4.

Subsequent gates, as shown in FIG. 4. are set at delay intervals corresponding to estimated or computed arrival times of reflections from individual layers in the specimen relative to the reference point.

The software embodied gating described here and hardware embodied gating are similar in nature in that both arrangements utilize gated window time delays to extract information from selected portions of a waveform. Either software or hardware gating could be used to embody the data sampling depicted in FIG. 4 of the drawings, however, programmed software gating is most easily controlled by an operator and provides more precise control of gate positions, gate widths and greater time stability. Software gating also utilizes less hardware and thereby reduces electrical noise and interference in an overall system. Software gating also tends to lower cost when a large number of gates are utilized; and is therefore the arrangement of choice in the present embodiment of the invention.

Frontal surface tracking is desirable in an ultrasonic energy waveform analysis system in order that smoothness variations in the workpiece surface not affect the images generated by internal features of the workpiece—because the initiation of the waveform digitization is fixed in time relative to the electronic trigger generated by the pulser/receiver (104 in FIG. 1). This time interval is determined by the relatively long transit time of the ultrasound between the piezoelectric transducer source and the workpiece. In the software of the present invention, the subroutine PROCG provides for varying the temporal position of the departure point 418 in order that surface variations and scan to scan misalignment of transducer and sample be ignored and waveform portions originating in the same physical feature of a workpiece be presented as a part of the same feature image for the workpiece. This frontal surface tracking involves the use of an algorithm which places the location of the waveform attainment of a predetermined threshold value in the initial measurable departure point of the waveform at 418 in FIG. 4.

The waveform information shown in FIG. 4 of the drawings wherein the amplitude of an ultrasonic reflection radio frequency (RF) signal is displayed as a function of time has become known as an A-scan display. This and other waveform displays, as shown in the following Table 1 are recognized in the ultrasonic testing and display arts.

TABLE 1

| | Display Nomenclature |
|---|---|
| A-Scan | Time (H) vs Amplitude (V) (Grey Scale not used) |
| B-Scan | Distance (H) vs Time (V) (Grey Scale is amplitude) |
| C-Scan | X position (H) vs Y position (V) (Grey Scale is amplitude) |

Figure 5:
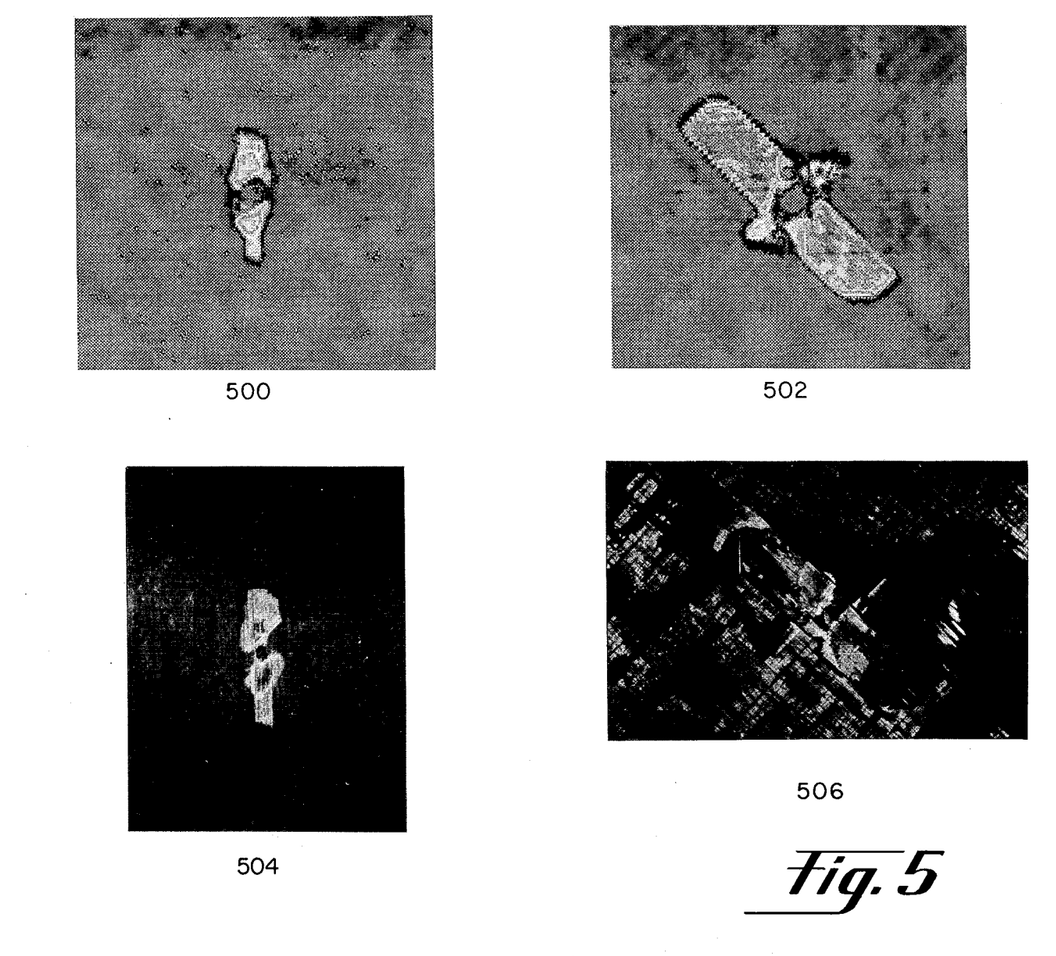
FIG. 5 shows a comparison between sonic wave images of a workpiece fault and photographic images of the same faults.

C-Scan presentations of internal features of a workpiece are a desired endpoint for the present system, presentations of this type are shown at 500 and 502 in FIG. 5 of the drawings with each image shown therein representing detected internal features at one layer or one plane of depth within a workpiece.

To implement a FIG. 4 based software waveform analysis and obtain a software gated C-scan, a front surface tracking threshold value, a reference point time location, and window gate delay starting and ending times must be defined by the operator. As a first step in this process, an RF A-scan sample of the specimen, that is a preliminary A-scan view of the specimen or workpiece, is digitized and its waveform displayed on an operator's cathode ray tube monitor. This preliminary A-scan view need not involve scanning movement of the ultrasonic transducer. The operator then positions a movable electronic cursor to a point on the slope of the front surface echo of the waveform which represents the amplitude of a detection threshold that will indicate the location of the front surface of the specimen, the point 418 in the FIG. 4, waveform, for example. Through a combination of renumbering the selected threshold value in memory and comparing successive waveform values with this stored value, when the threshold value is exceeded the front surface tracking algorithm of the subroutine PROCG in the microfiche appendix program listing herein will define that point as the time location of the workpiece front surface. The location of the front surface tracking position is thereafter determined for each successive RF A-scan used in compiling the C-scan data. The front surface tracking arrangement of the subroutine PROCG, therefore, provides an adjustable software generated time delay relative to the initial electronic trigger signal for each RF A-scan to compensate for specimen curvature and misalignments of the scan axis to the orientation of the specimen as was explained above. This flexibility allows the software gates to view layers of consistent depth throughout the course of a C-scan data collection sequence.

The subroutine DEFP6 requires that the operator also define the polarity of the waveform involved in the threshold determination—as either positive or negative and also define the method of locating the threshold. Location may be defined either by comparing single points on the waveform to the threshold value or by calculating and comparing a two-point moving average value of the waveform to the threshold value. The moving average method is usually more desirable since it can be expected to eliminate false threshold detections due to random or single data point noise spikes in the waveform. Another important feature of the front surface tracking algorithm is an ability to detect defective A-scan data which results either from an incorrect digitizer 120 trigger, extreme amounts of noise or nonspecular reflection of the sound wave from the workpiece. If the front surface tracking threshold cannot be established successfully or if a threshold value is found so late in time that it would cause the last of the software gates to not be included in the digitized a-scan area, then the scanning movement is stopped in the subroutine COYADC and the preliminary A-scan data is redigitized up to 10 times in an effort to obtain a correct threshold placement. If all such attempts fail, then the operator is notified and asked if the scan should be aborted or if data from the previous correct A-scan should be substituted for the current A-scan data and the scanning continued. These checks add a factor of confidence to the validity of the software gated data.

After the parameters for front surface tracking are established, the reference point R at 414 in the FIG. 4 waveform 400 is to be defined. A reference point is utilized because it is more convenient to relate gate locations to the peak value of the front surface echo (or some other feature of the A-scan which will be reproduced in subsequent echoes from features of interest in the workpiece) than to the location of the front surface tracking threshold. The reference point is utilized in the subroutines SPECG, PROCG AND SGATE as the zero point for computing the center line positions of the software gates which follow. The reference point is defined by the operator as a fixed time delay after the front surface tracking position and is determined by moving an electronic cursor along the waveform to the desired position and depressing an operator's entry key of the computer 100.

Once the reference point R at 414 is located, the operator may select the number of software gates desired for the scan. This may be any number from 1 to 160 software gates in the arrangement of the subroutine DEFP6 shown herein. Gate locations may be determined by any of several methods. One method for example, allows the operator to move an electronic cursor along the waveform and depress a key at the desired starting and ending points for each software gate. The gates can be in any location along the waveform and can be of any width and can overlap if desired. Another method locates the software gates by calculating time delays in nanoseconds from the reference point. The operator can enter the times for desired gate location and width in nanoseconds for each individual gate or can specify equal spacing between all gates and the width of all gates in a single command as is indicated in the subroutine SPECG and MENUA listing. For example, in a workpiece which consists of a 32 ply panel the number of gates might be set to 32 and the reference point set at the peak of the front surface echo. In such an arrangement, the spacing between gates is then set to the round trip travel time between adjacent ply interfaces, and the gate widths set to a narrow range (i.e. 10–30 nanoseconds) falling within the individual plys. Usually 512 data points are digitized in each A-scan (e.g. two to six data points digitized in each of the 32 ply located gate windows of the example) and when the scan is completed the result will be 32 data files with each file defining the image of a C-scan display—a layer sample of the workpiece. The A-scan data point information is not required to be saved after the window gate samples are stored, the samples of the lines 420–432 in FIG. 4 are selected and captured; this, of course, results in a considerable saving of disk and memory space.

One of several methods may also be selected to compute the effective data value to be stored for each of the software gates. These methods are recited in the subroutine DEFPG and calculated in subroutine PROCG herein and include use of mean value, peak value, minimum value and peak-to-peak values of the data points within the gate time interval, peak or minimum value is, for example, most often the reduction algorithm of choice in detecting delaminations in a workpiece. In the example shown in FIG. 4, minimum value is used. This choice was made because the reference peak 436 is positive and reflections from delaminations must be out of phase or contain negative peak values relative to the reference. This is illustrated in waveform 450 in FIG. 4. The flaw in layer three produces a large negative sample amplitude 458 compared to the original small positive value 426 shown in the reference. The changes in the other flaw sample amplitudes 454, 456, 460, 462, and 464 are much smaller relative to the reference values 422, 424, 428, 430, and 432. The location of the gate containing the largest change defines the layer or depth of the delamination or defect. The number of data points within a gate time interval is determined by the width of the gate in nanoseconds divided by the waveform analyzer digitizing interval which in the present example is the five nanoseconds e.g. a (200 MHz digitizing rate).

The minimum and maximum data values residing in each of the 32 data files of the above example are also identified by the subroutine BIOCON and stored for utilization later by the C-scan display program in order to obtain the maximum benefit from the grey level capability of the display device selected—i.e. to maximally utilize the grey level range of the monitor 108 or the printers 116 and 118 in FIG. 1. This expansion of data range occurs in the subroutine DISPLA in the present embodiment of the invention.

As an example of this data range expansion, in the present example, the initially digitized waveforms have been stated to have a maximum of eight bits or 256 discrete levels of amplitude resolution in the selected LeCroy transient waveform recorder. In many instances, however, the information received from a workpiece may occupy only, for example, 20 levels of this dynamic range. By expanding this 20 level limited range of to cover the available dynamic range of the display device, or at least a significant portion thereof, the present invention apparatus is capable of displaying C-scan images relating to workpiece internal features that would have been totally obscured by prior art signal processing arrangements. In this expansion arrangement, for example, differences between the waveforms 400 and 450 in FIG. 4, in particularly differences between the fourth gate samples at 426 and 458 would be emphasized in a C-scan image.

As indicated by the drawing legend attending the sample 450 in FIG. 4, this view relates to a third layer flaw in the workpiece so that large differences between the fourth gate sample at 458 and the fourth gate sample at 426 in the view 400 exist. In view of the data expansion in the subroutine DISPLA just prior to displaying, these large variations in peak amplitude will occupy a large portion of the display device dynamic range.

The ability to see small variations in large amplitude processed data and maximally apportion the available display dynamic range to these small differences—that is ability to resolve differences between waveform samples that are nearly equal in value is a significant aspect of the present invention. Situations of this kind are frequently found in ultrasonic data when the sample layer of interest is located proximate to a large echo region of the sample

SOFTWARE

The software used in the preferred embodiment of the invention is, as has been stated, reproduced in the microfiche appendix to the present document. This software consists of a main program and 64 dedicated purpose subroutine—several of which have been referred to in the above description material. This software makes use of the known Fortran high level programming language. The command statements in this language incorporate significant amounts of human readable symbols and text. In the microfiche appendix, the main program and each subroutine is provided with a hand-written routine identification number in the upper righthand corner of the appendix page—a number which is encircled. Each page of the software is also provided with a lower righthand corner page number which is underlined. In addition to the programming commands which are somewhat human readable as well as operating system readable, each routine in the program listing includes commentary statements which indicate the purpose of the routine the function being performed by a following group of programming statements and other information. The commentary statements are indicated by the preliminary letter C in the program listing such comments are, of course, ignored by the computer operating system. The purpose of later added modifications to the software is also recited in the heading of each routine.

Figure 6:
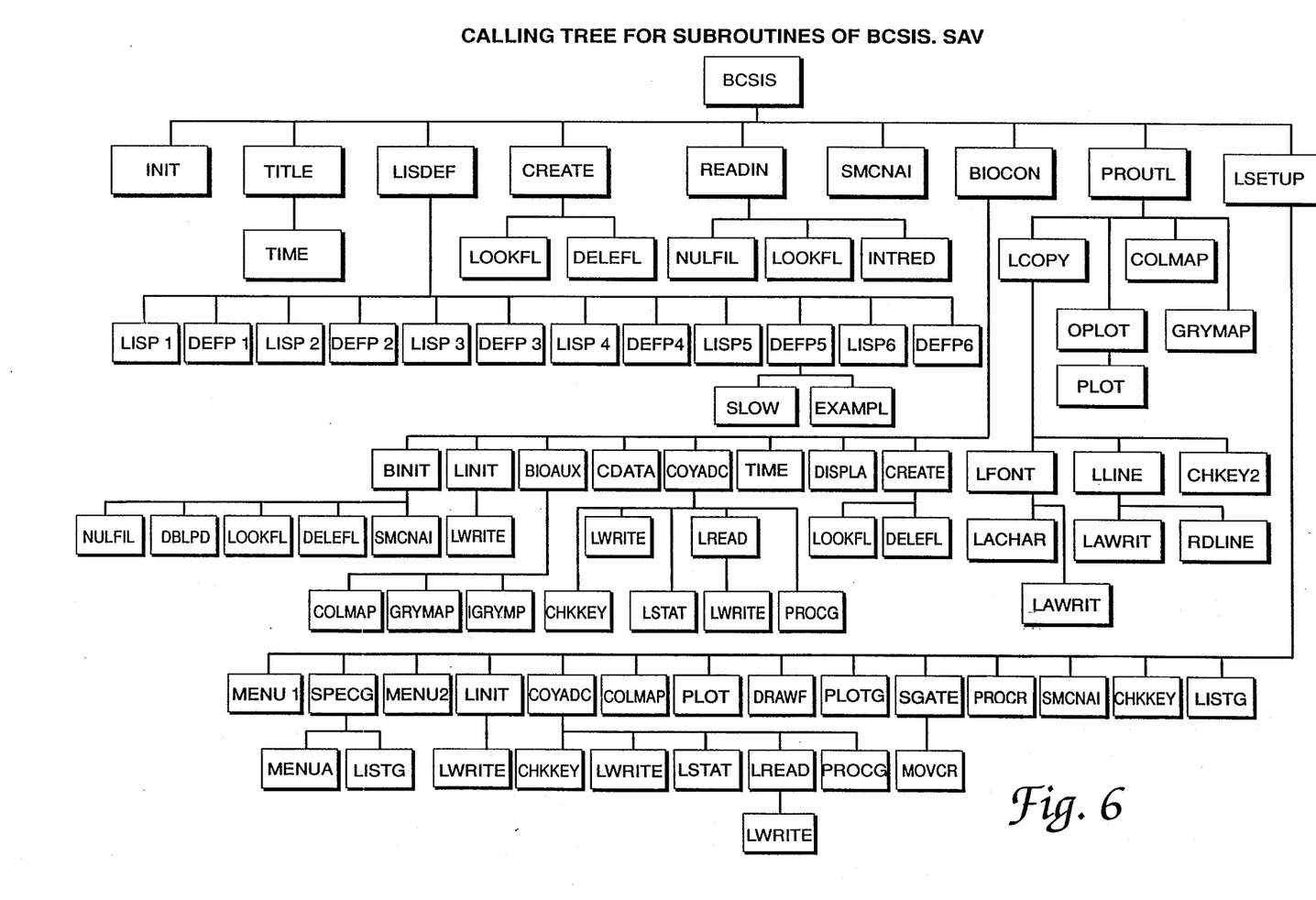
FIG. 6 shows a calling tree diagram for the computer subroutines of the described system.

A calling tree diagram for the 64 subroutines used in the main program BCSIS of the software is shown in FIG. 6 of the drawings. The calling tree diagram indicates the sequence in which the disclosed subroutines are called in executing the main program—and aids in understanding the functions of both the main program and the subroutines. The calling tree diagram does not include about 75 calls to library function subroutines which also occur in the main diagram and subroutines. These library function subroutines are identified in the program listing and involve operations which are known to persons skilled in the computer software art. Library function subroutines of these types are commonly available in the software commercial marketplace. The library subroutines include LSPLIB a system library routine. IBV2DP and IBUP IEEE-488 GPIB data transfer libraries, a virtual array handler library VRTARY, a terminal data entry and message display library, SVTL1B, and GRAPHL1, GRAPHL2, CHTABL and CG2 color graphics display libraries.

Subroutines in the calling tree diagram are called proceeding from left to right on each level or horizontal line of the drawing. However, in instances where a subroutine has a subtree under it, then each subroutine in the entire subtree is called before proceeding to the next subroutine on the original level. The calling tree does not recite the conditions required for a subroutine to be called or how many times a subroutine is called by another subroutine. For example, some routines are operator selectable while others are always called, and subroutines such as INIT are called only once while others like LREAD are called several hundred thousand times during a complete C-scan.

The purpose and operation of the nine top level subroutines called from the main program BCSIS is generally as follows:

INIT—Initializes variables to their default conditions for commencing operations of the program.

TITLE—Displays the program version number, date, time, etc., on the operator's terminal.

LISDEF—Displays six pages of setup parameters and the general information required to operate a C-scan, and asks the operator to enter needed decisions.

CREATE—Creates a data control file which stores on disk the six pages of setup information.

READIN—Reads a control data file from disk and inserts the data into the six pages of setup information.

SMCNAI—Allows operator energizing of the motors controlling the carriage and thus positions the ultrasonic transducer to any desired position.

BIOCON—C-scan data collection subroutine - selected by the operator after all LISDEF setup information is correct and after the software gates are setup by the routine LSETUP. BIOCON causes the motors to scan each line and to stop at each data collection point, collect RF data from the digitizer (COYADC and LREAD routines), perform front surface tracking and process the raw RF data into the data specified by each software gate (PROCG), store the data on disk (BIOCON), add a line to the color graphics display (DISPLA) and at the end of the entire scan create a control file for each software gate (CREATE).

PROUTL—A operator selectable subroutine graphics screen to either a laser printer or to a color printer. It can also display plots of raw RF data and can select color maps for the graphics display.

LSETUP—provides for setup of the software gates. It collects and processes raw RF data (COYADC), plots RF data and front surface tracking information on the graphics screen (PLOT, DRAWF and PLOTG) and lists gate setup information (LISTG). Then, LSETUP allows the operator to set the gate positions by either moving a cursor on the RF graphics displaY to the desired starting and ending positions (in time) of the gate (SGATE) or by specifying the center position and width (in nanoseconds) of each gate (SPECG).

The combination of the FIG. 6 calling tree diagram, the above description of the nine major subroutines used in the computer program, the purpose statements included in the microfiche listing for each subroutine, the comment statements in the microfiche listing, and the preceeding verbal description of the invention are believed to be more than adequate for the purpose of conveying an understanding of the software and other aspects of the invention to persons skilled in the ultrasonic scanning and computer art.

RESULTS

The software gated ultrasonic echo imaging of the present invention is capable of achieving good correlation with the physical manifestations of impact damage in laminate test specimens in a laboratory test arrangement. The views 500 502. 504, and 606 in FIG. 5 of the drawings show comparisons between ultrasonic scanning images, the images at 500 and 502 and microphotograph of the same test specimen taken during successive steps of physically removing sample laYers. Correlation can be observed in comparing the scanning image at 500 with the physical image at 504, and includes the general shape, size, orientation and other features of the damage area. The diagonal cross hatch background in the view 504 in FIG. 5 results from the photographic process and the woven fiber nature of the laminate material tested. Additional microphotograph results and discussions relating to the invention is to be found in the published article *Characteristic of Impact Damage in Composites* written by present inventors, C. F. Buynak, T. J. Moran, and a third colleague, and appearing in the periodical *Official Journal of the Society for the Advancement of Material and process Engineering* (SAMPE Journal) Vol. 24, No. 2, March/April 1988 and the article "Characterization of Impact Damage in Composites" by C. F. Buynak and T. J. Moran, appearing at pages 1203-1211 in the textbook *Review of Progress in Quantitative Nondestructive Evaluation* published by plenum press, New York. Although the contents of these articles are deemed to be non essential material with respect to the present patent disclosure, the contents are hereby incorporated by reference herein.

While the apparatus and method herein described constitute a preferred embodiment of the invention, it is to be understood that the invention is not limited to this precise form of apparatus or method, and that changes may be made therein without departing from the scope of the invention, which is defined in the appended claims.

We claim:

1. A reflected energy process for optimized nondestructive ultrasonic acoustic mapping of internal details, including subsurface defects, within a workpiece comprising the steps of:
    illuminating a selected portion of said workpiece with an acoustic energy raster of scan lines that include pulses of ultrasonic frequency acoustic energy of first time interval separation along said raster scan lines;
    sensing the ultrasonic frequency ringing waveform energy return echoes from said workpiece received pulses of acoustic energy during an echo time interval following each illuminating pulse;
    sampling selected points of said ringing waveform during a plurality of number identifiable data acceptance window gates of second time interval width and third time interval successive separations during each said echo time interval following said illuminating pulses, said sampling including digitizing a predetermined number of waveforms values within each window gate time interval;
    generating from said plurality of waveform values in each window gate, and using a predetermined value consolidation algorithm, a pixel value that is representative of said plurality of waveform values in the window gate;
    assembling the pixel values from similar member identifiable window gates in each echo time interval into video images, each image thereby describing the acoustic energy reflection pattern from a plane of different subsurface depth in said workpiece;
    adjusting, from a viewing of said video images, the parameters of said process including the workpiece portion selected for illumination, the duration and amplitude of said illuminating pulses, the number of digitized waveform values in each window gate, the duration of said first second and third time intervals and said value consolidation algorithm to obtain a better view of selected details including said subsurface defects in said workpiece;
    repeating said illuminating, sensing, sampling, generating, assembling, and adjusting steps until optimum views of selected workpiece details obtain;
    recording the pixel values and locations comprising said optimum views.

2. The process of claim 1 wherein said illuminating with a scanning raster includes physical movement of an electrical energy-acoustic energy transducer element.

3. The process of claim 1 wherein said sampling step includes digitizing signal amplitudes from a plurality of points within each window gate time interval.

4. The process of claim 1 wherein said value consolidation algorithm is selected from the algorithms group comprised of a peak to peak difference measuring algorithm, a mathematical average of sample values algorithm, a peak value responsive algorithm, and a minimum value responsive algorithms.

5. The process of claim 1 wherein said sampling step includes locating said window gates within said echo time interval by time measurement initiated from a predetermined ringing waveform excursion representation of the illuminated frontal surface portion of said workpiece.

6. A method for processing the acoustic echo electrical waveform information from an ultrasonic energy scanning apparatus to resolve near surface and internal physical features of a scanned sample comprising the steps of:
   transmitting and receiving ultrasonic energy in communication with said sample using electrical to acoustic energy transducer means of characteristic electrical ringing rate which lies in the high radio frequency portion of the electromagnetic spectrum;
   sampling individual of the high radio frequency ringing rate waveform excursions in the electrical output of said transducer means during a succession of sample time slots disposed in accordance with a predetermined time organized sampling criteria; and
   assembling the corresponding time slot samples from a plurality of scans of said sample into arrays of sample layer descriptive data.

7. The method of claim 6 further including the steps of:
   determining the dynamic amplitude range of said samples in each said array; and
   displaying the visual image represented by each said array with the dynamic range of the visual image maximally apportioned to the array dynamic amplitude range.

8. The method of claim 6 wherein said time organized sampling criteria is referenced to a predetermined portion of said electrical waveform.

9. The method of claim 6 further including the step of optimizing said sampling of waveform excursions with respect to the view of said internal physical features represented by said arrays of sample layer descriptive data.

10. The method of claim 6 further including the step of physically moving said transducer element to accomplish scanning of said sample.

11. The method of claim 10 further including the step of acoustically coupling said transducer element with said sample using a liquid energy transmission medium.

12. The method of claim 8 wherein said predetermined electrical waveform portion comprises a waveform portion descriptive of an external feature of said scanned sample.

13. The method of claim 12 wherein said predetermined electrical waveform portion is the portion describing the surface of said sample.

14. The method of claim 12 wherein said sampling criteria includes a plurality of sampling window gate time intervals and wherein said sampling window gate time intervals commence upon expiration of a predetermined delay interval initiated by the sample near surface reflection first waveform excursion from quiescent value.

15. Optimized ultrasonic mapping apparatus comprising:
   transducer means for both illuminating a selected portion of a workpiece with a scanning raster that includes pulses of acoustic energy of first time interval separation between the points comprising each raster line and for sensing the ultrasonic frequency ringing waveform energy return echoes from said pulses of acoustic energy during an echo time interval following each illuminating pulse;
   means for sampling the individual excursions of said ringing waveform during a plurality of number identifiable data acceptance window gates of second time interval width and third time interval successive separations during each said echo time interval following said illuminating pulses, said sampling including digitizing a predetermined number of segregated waveform values within each said window gate;
   apparatus for generating from said plurality of waveform values in each window gate, and in accordance with a predetermined value determining algorithm, a pixel value representative of said plurality of waveform values within the window gate;
   means for altering the parameters of said process, including the workpiece portion selected for illumination the time duration of said illuminating pulses, the number of digitized waveform values in each window gate, the duration of said first second and third time intervals and the nature of said value determining algorithm, in iterative sequence until an optimum view of selected workpiece details including said subsurface defects obtains;
   said means for altering including apparatus for viewing assembled images of said pixels;
   apparatus for recording and identifying optimized pixel images.

16. The apparatus of claim 15 wherein said transducer means comprises a single bilateral transducer.

17. The apparatus of claim 16 wherein said value determining algorithm is selected from the group of algorithms which includes a time averaging algorithm, a peak value responsive algorithm, a minimal value algorithm and a peak to peak responsive algorithm.

18. The apparatus of claim 17 wherein said means for viewing includes a predetermined display dynamic range and means for maximally apportioning said display dynamic range to the overall dynamic range of the pixel values in each image to be viewed.

19. The apparatus of claim 18 wherein said means for sampling, and said means for generating a representative pixel value each include a programmable digital computer.

20. The apparatus of claim 19 wherein said third time interval is negative in time value and represents the overlapping of adjacent of said window gates.

21. The method of ultrasonic mapping of surface adjacent internal defects in a workpiece comprising the steps of:
   recording individual amplitude values from the radio frequency ringing waveform echoes generated by acoustic energy scanning of said workpiece;
   identifying the waveform echo time regions relating to said surface adjacent defects in said recorded sample values;
   determining the amplitude range of the waveform samples located within said selected echo time regions;
   apportioning the available dynamic range of a video display apparatus over said amplitude range of said echo time regions waveform samples;
   whereby large waveform amplitude values relating to external surface echoes in said ringing waveforms are suppressed and the adjacent or coincident in time small amplitude values relating to said external surface adjacent defect are resolved in an image presented by said video display apparatus.

22. Electronic signal processing aircraft surface structure inspection apparatus of limited memory storage requirements for use in an aircraft operations facility comprising the combination of:

electrical to acoustic signal transducer means for bidirectionally communicating pulsed ultrasonic frequency reflection mode acoustic energy with selected small physical regions of said aircraft surface structure and for converting the surface structure reflected acoustic signals into echo electrical signals;

electronic sampling means timewise located along said echo electrical signals in response to the locus of previously determined thickness regions of aircraft surface structure inspection interest, for extracting time selected representative sample portions from said echo electrical signals;

predetermined algorithm controlled means responsive to one of the sample portion effective data computing algorithms taken from the group comprising, a mean value computing algorithm, a peak value sensing algorithm, a minimum value sensing algorithm and a peak to peak value sensing algorithm for generating pixel determining output signals representative of said echo signals sample portion, said generated pixel determining output signals being of reduced memory storage requirements with respect to both said echo signals and said echo signals sample portions;

memory means for storing pixel determining output signals;

display means for assembling said pixel determining output signals into images representative of said regions of aircraft surface inspection interest.

* * * * *

UNITED STATES PATENT AND TRADEMARK OFFICE
CERTIFICATE OF CORRECTION

PATENT NO. : 4,947,351

DATED : August 7, 1990

INVENTOR(S) : Thomas J. Moran et al

It is certified that error appears in the above-identified patent and that said Letters Patent is hereby corrected as shown below:

IN THE ABSTRACT, line 5, ---impractical--- should precede "images".

Col 1, line 67, "waVe" should read ---wave---.
Col 3, line 20, "resting" should read ---testing---.
Col 3, line 62, "lank" should read ---tank---.
Col 4, line 13, after "FIG. 1" --a period-- should be inserted
Col 4, line 34, "pr®determined" should read ---predetermined---.
Col 5, line 5, "K" should be deleted.
Col 5, line 13, after "108" a comma should be inserted.
Col 5, line 24, after "description" a period should be inserted.
Col 5, line 33, "is" should be deleted.
Col 5, line 37, "mounted" should be deleted.
Col 7, line 10, "such" should read ---much---.
Col 7, line 39, "string" should read ---strong---.
Col 7, line 65, "405" should read ---450----.
Col 8, line 62, after "108", a comma should be inserted.
Col 8, line 64, "tWo-step waVeform" should read ---two-step waveform---.
Col 8, line 68, after "apparatus" a comma should be inserted.

UNITED STATES PATENT AND TRADEMARK OFFICE
CERTIFICATE OF CORRECTION

PATENT NO. : 4,947,351

DATED : August 7, 1990

INVENTOR(S) : Thomas J. Moran et al

It is certified that error appears in the above-identified patent and that said Letters Patent is hereby corrected as shown below:

Col 9, line 21, after "FIG. 4" a comma should be inserted.
Col 10, line 60, the comma should be a period and "presentations" should be capitalized.
Col 11, line 57, after "aborted" a comma should be inserted.
Col 12, line 51, the first comma should be a period and "peak" should be capitalized.
Col 13, line 55, "subroutine" should read ---subroutines---.
Col 14, line 6, after "listing" a comma should be inserted.
Col 15, line 6, after "subroutine" ---to copy the color--- should be inserted.
Col 15, line 17, "displaY" should read ---display---.
Col 15, line 37, after "500" a comma should be inserted.
Col 15, line 37, the first period should be a comma.
Col 15, line 37, "606" should be ---506---.
Col 15, line 39, "microphotograph" should read ---microphotographs---.
Col 15, line 41, "laYers" should read ---layers---.
Col 15, line 54, "process" should read ---Process---.
Col 15, line 59, "plenum press" should read ---Plenum Press---.

UNITED STATES PATENT AND TRADEMARK OFFICE
CERTIFICATE OF CORRECTION

PATENT NO. : 4,947,351

DATED : August 7, 1990

INVENTOR(S) : Thomas J. Moran et al

It is certified that error appears in the above-identified patent and that said Letters Patent is hereby corrected as shown below:

Col 16, line 23, "waveforms" should read ---waveform---.

Col 16, line 30, "member" should read ---number---.

Col 16, line 62, "algorithms" should read ---algorithm---.

Col 18, line 15, after "illumination" a comma should be inserted.

Signed and Sealed this

Twelfth Day of January, 1993

Attest:

DOUGLAS B. COMER

Attesting Officer

Acting Commissioner of Patents and Trademarks